United States Patent
Israel

(12) 
(10) Patent No.: US 6,881,217 B2
(45) Date of Patent: Apr. 19, 2005

(54) STENT ASSEMBLY

(76) Inventor: Henry M. Israel, 39 Ben Zakai Street, Bnei Brak 51482 (IL)

( * ) Notice: Subject to any disclaimer, the term of this patent is extended or adjusted under 35 U.S.C. 154(b) by 209 days.

(21) Appl. No.: 09/935,173

(22) Filed: Aug. 23, 2001

(65) Prior Publication Data

US 2002/0045932 A1 Apr. 18, 2002

Related U.S. Application Data

(60) Provisional application No. 60/239,923, filed on Oct. 13, 2000.

(51) Int. Cl.$^7$ .............................................. A61B 17/22
(52) U.S. Cl. ...................... 606/200; 623/1.15; 623/1.16
(58) Field of Search .............................. 623/1.15, 1.22, 623/1.16; 606/200

(56) References Cited

U.S. PATENT DOCUMENTS 4,893,623 A  *  1/1990  Rosenbluth ................. 606/192
5,246,445 A  *  9/1993  Yachia et al. ............... 606/108
5,575,818 A  *  11/1996 Pinchuk ......................... 623/1
5,836,966 A  *  11/1998 St. Germain ................ 606/198
6,524,333 B1 *  2/2003  Claren et al. .............. 623/1.11
6,676,682 B1 *  1/2004  Tsugita et al. .............. 606/200

* cited by examiner

Primary Examiner—Michael H. Thaler
(74) Attorney, Agent, or Firm—Dekel Patent Ltd.; David Klein

(57) ABSTRACT

A stent assembly including an upstream portion adapted to modify a flow characteristic of embolic material disposed in a blood stream flowing through the upstream portion, and a downstream portion in fluid communication with the upstream portion and adapted for the blood stream to flow therethrough, the downstream portion including a trapping region for trapping therein the embolic material. The downstream portion may extend from the upstream portion, or alternatively, may be distanced from the upstream portion.

2 Claims, 1 Drawing Sheet

STENT ASSEMBLY

This application claims the benefit of provisional application No. 60/239,923 filed Oct. 13, 2000

FIELD OF THE INVENTION

The present invention relates generally to stent assemblies and particularly to a stent assembly adapted to filter and trap embolic material.

BACKGROUND OF THE INVENTION

Stenosis within arteries and other blood vessels may be treated by permanently or temporarily introducing a stent into the stenosed region to open the lumen of the vessel. The stent may be introduced into the desired blood vessel using known percutaneous or transluminal methods. A catheter, having the stent securely crimped thereon, may be directed to the region of the blood vessel being treated. The catheter may be positioned such that the stent is centered across the stenosed region. Balloon inflation may then be used to expand the stent radially, thereby engaging the stenosed material. As the stent expands, the material is forced outward, dilating the lumen of the blood vessel. Due to the substantial radial force of the stent construction, the stent retains its expanded shape, providing an open passage for blood flow. The balloon is then deflated and the catheter withdrawn.

A stent may be typically constructed from a mesh or coiled material. Stenotic material trapped between the stent and the vessel wall may extend into the openings in the mesh or coil, and may be sheared off by the longitudinal compression of the stent to create loose embolic debris. When this material travels downstream, it can cause serious complications. For example, loose embolic material released within the ascending aorta, the aortic arch, or the carotid arteries may travel downstream to the brain, possibly causing stroke, which can lead to permanent injuries or even death of the patient.

In-line filters, such as mesh or mesh wire filters, have been used to attempt to filter embolic material downstream of the stent. A drawback of such filters is that they generally are not compatible with previously known delivery devices. Another drawback is that with time the filter fills and degrades in performance or occludes the lumen.

SUMMARY OF THE INVENTION

The present invention seeks to provide a stent assembly that filters and traps embolic material, thereby preventing such material from flowing downstream and possibly posing a danger to the patient.

In one embodiment of the present invention, the stent assembly comprises two portions. In a first upstream portion, the stent assembly may be shaped and constructed so as to separate embolic material from the rest of the blood flow. In a second downstream portion, the stent assembly may be shaped and constructed to trap any embolic material separated by the first portion.

The present invention may prevent embolic material from escaping a site of intervention within the aorta, the carotid arteries, and other arteries generally, thereafter causing damage to vital organs, such as the brain. The invention may be suitable for introducing a stent into a region of a major blood vessel within the human body having plaque deposits, such as but not limited to, the ascending aorta, the descending aorta, aortic arch, common carotid artery, external and internal carotid arteries, brachiocephalic trunk, middle cerebral artery, anterior cerebral artery, posterior cerebral artery, vertebral artery, basilar artery, subclavian artery, brachial artery, axillary artery, iliac artery, renal artery, femoral artery, popliteal artery, celiac artery, superior mesenteric artery, inferior mesenteric artery, anterior tibial artery, and posterior tibial artery.

There is thus provided in accordance with an embodiment of the present invention a stent assembly including an upstream portion adapted to modify a flow characteristic of embolic material disposed in a blood stream flowing through the upstream portion, and a downstream portion in fluid communication with the upstream portion and adapted for the blood stream to flow therethrough, the downstream portion including a trapping region for trapping therein the embolic material. The downstream portion may extend from the upstream portion, or alternatively, may be distanced from the upstream portion.

In accordance with an embodiment of the present invention the upstream or downstream portion includes a cross-sectional area that varies along an axial portion of the stent assembly.

Further in accordance with an embodiment of the present invention the upstream portion includes a downstream convergence.

Still further in accordance with an embodiment of the present invention the trapping region has a greater cross-sectional area than a downstream end of the upstream portion.

In accordance with an embodiment of the present invention the trapping region includes a divergent portion of the downstream portion.

Further in accordance with an embodiment of the present invention the trapping region is in an upstream portion of the downstream portion.

In accordance with an embodiment of the present invention the upstream portion includes a plurality of coils or meshwork.

Further in accordance with an embodiment of the present invention the coils or meshwork have a coverage that varies along an axial portion of the stent assembly.

Still further in accordance with an embodiment of the present invention the coils or meshwork have a thickness that varies along an axial portion of the stent assembly.

Additionally in accordance with an embodiment of the present invention the coils or meshwork are adapted to impart a radial force to a lumen in which the stent assembly is placeable, wherein the radial force varies along an axial portion of the stent assembly.

In accordance with an embodiment of the present invention a restrictor element is disposed in at least one of the upstream and downstream portions, the restrictor element being adapted to limit expansion of the at least one of the upstream and downstream portions.

Further in accordance with an embodiment of the present invention at least one of the upstream and downstream portions includes an anti-thrombogenic agent.

Alternatively, in accordance with an embodiment of the present invention, at least one of the upstream and downstream portions includes a thrombogenic agent.

Still further in accordance with an embodiment of the present invention at least one of the upstream and downstream portions includes a friction-enhancing material.

Alternatively, in accordance with an embodiment of the present invention, at least one of the upstream and downstream portions includes a friction-reducing material.

In accordance with an embodiment of the present invention the upstream portion is placeable in a blood vessel upstream of a bifurcation in a blood vessel system, the bifurcation including a first downstream path and a second downstream path, the downstream portion being placeable in the second downstream path, and a space between the downstream portion and the upstream portion is alignable with the bifurcation, such that blood flows to both the first and second downstream paths with embolic material being trapped in the trapping region.

BRIEF DESCRIPTION OF THE DRAWINGS

The present invention will be understood and appreciated more fully from the following detailed description taken in conjunction with the appended drawings in which.

DETAILED DESCRIPTION OF THE PRESENT INVENTION

Figure 1:
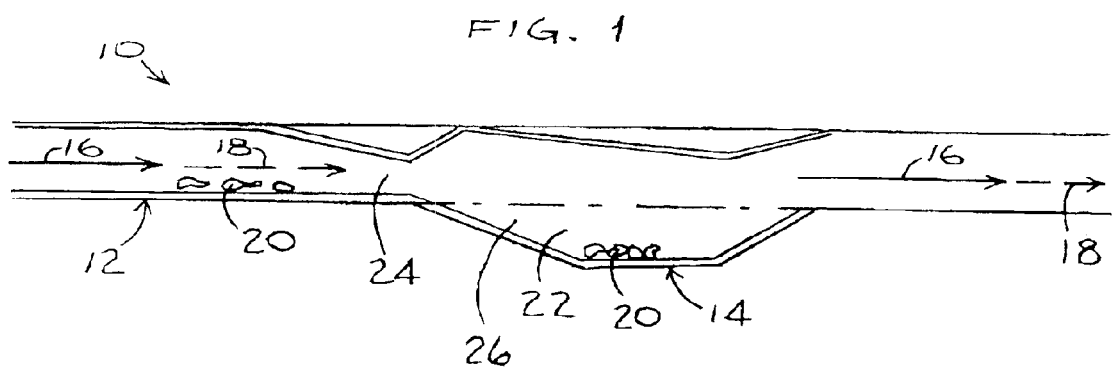
FIG. 1 is a simplified illustration of a stent assembly constructed in accordance with an embodiment of the present invention in a deployed state in a blood vessel.

Reference is now made to FIG. 1, which illustrates a stent assembly 10 constructed in accordance with an embodiment of the present invention.

Stent assembly 10 preferably includes an upstream portion 12 and a downstream portion 14 in fluid communication with upstream portion 12. Both upstream and downstream portions 12 and 14 are adapted for a blood stream 16 to flow therethrough. Blood stream 16 may include a non-embolic flow portion 18 including substances, such as but not limited to, erythrocytes, leucocytes and plasma, and embolic material 20 disposed in the blood stream. Embolic material 20 may have entered the blood stream 16 by loosening from the blood vessel wall. Downstream portion 14 preferably comprises a trapping region 22 for trapping therein embolic material 20, as is described more in detail hereinbelow. Trapping region 22 may be in an upstream portion of downstream portion 14. Upstream portion 12 is adapted to modify a flow characteristic of embolic material 20 flowing therethrough so as to cause embolic material 20 to flow to trapping region 22 and be trapped therein, while the non-embolic flow portion 18 of the blood stream 16 continues to flow freely through downstream portion 14, as is described more in detail hereinbelow.

In the embodiment of FIG. 1, downstream portion 14 extends from upstream portion 12. However, downstream portion 14 may be separate from upstream portion 12, as is described further hereinbelow with reference to FIG. 2.

As seen in FIG. 11 the trapping region 22 may include a divergent portion that is asymmetric about the longitudinal axis comprising a region in which the divergent portion converges towards the longitudinal axis on one side thereof (e.g., the top side as shown in FIG. 1) and on an opposite side thereof (e.g., the bottom side as shown in FIG. 1) diverges away from the longitudinal axis.

The cross-sectional area of upstream portion 12 or downstream portion 14 may vary along an axial portion of stent assembly 10. For example, upstream portion 12 may comprise a downstream convergence 24 and trapping region 22 may comprise a divergent portion 26. Trapping region 22 may have a greater cross-sectional area than the downstream end of upstream portion 12. The convergence 24 preferably modifies flow characteristics of the non-embolic flow portion 18 and the embolic material 20 disposed in the blood stream 16, and thereby separates the embolic material 20 from the non-embolic flow portion 18.

The particular shape shown in the illustrated embodiments may be constructed in a variety of manners. Reference is now additionally made to FIG. 3, which illustrates an exemplary construction, although it is understood that the invention is not limited to the illustrated construction. Upstream and downstream portions 12 and 14 may be constructed as coiled stents comprising a plurality of coils 28. Alternatively, the same illustration may comprise a meshwork stent assembly comprising a plurality of mesh portions 28 separated from each other by spaces. The description follows for coils 28, but it is understood that the description applies as well for a meshwork. In general, the coils or meshwork are characterized by a "coverage", meaning the ratio between the solid portion of the coils or meshwork to the spaces therebetween.

A coiled stent provides controllable force over its axial length. Such a stent may be formed by rolling a mesh or wire into a tube aligned with the axis of the tube. The stent may be generally formed of a resilient, biocompatible material, such as spring steel or a nickel-titanium alloy, and may be designed to be highly crush resistant. The coiled stent may be introduced percutaneously and transluminally with small delivery diameters, high crush resistance, low migration potential and ease of deployment.

The coils 28 may impart an unequal radial force over an axial portion of the stent assembly 10 to provide a controlled shape. The force profile over the axial portion may be produced, for example, by a non-uniform spacing of the coils 28 (as indicated by arrows 30) or by a non-uniform thickness of the coils 28 (as indicated by arrows 32) over the axial length. The controlled shape may produce a flow of the blood stream 16 through the stent assembly 10 (which flow may be laminar or non-laminar, with no cavitations), in such a manner as to produce different particulate velocities. The different particulate velocities may be a function of particle size. For example, erythrocytes and leucocytes are membrane-enclosed fluids with different flow characteristics (e.g., density and viscosity) than the more rigid structure and unique density of embolic material 20, e.g., micro-emboli or other similar material. The non-embolic flow portion 18 may thus be separated from the embolic material 20, since the embolic material has a larger particle size.

The coils 28 in upstream or downstream portion 12 or 14 may be of uniform or non-uniform shape. As mentioned hereinabove, trapping region 22 may have a greater cross-sectional area than the downstream end of upstream portion 12.

The coils 28 may lie parallel to or on the lateral dimension of delivery apparatus (not shown) when configured for delivery, and expand radially outward when deployed. For example, the coiled stent assembly 10 may be percutaneously and transluminally delivered by rolling the stent assembly 10 to a small diameter and inserting it into a constraint, e.g., a sheath (not shown), which retains the stent in the contracted state. After delivery of the coiled stent assembly 10 to the implantation site, the constraint (e.g., sheath) may be removed, allowing the stent assembly 10 to unroll. The stent assembly 10 may be further expanded into position using a conventional balloon dilatation device, for example.

Figure 3:
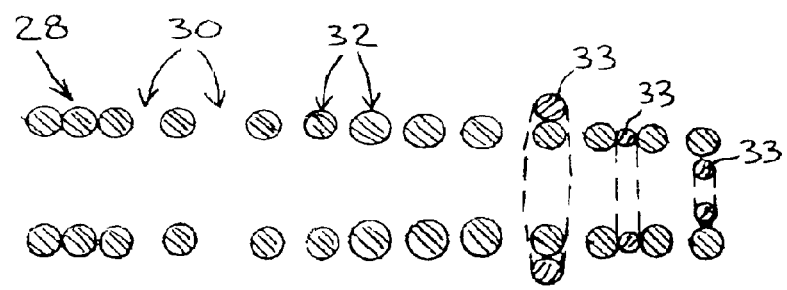
FIG. 3 is a simplified sectional illustration of the stent assembly of FIG. 1 or 2, constructed of a plurality of coils or meshwork in accordance with an embodiment of the present invention.

Expansion of the stent assembly 10 may be constricted, limited or restrained so as to obtain a converging or diverging (or any other arbitrary) shape. For example, as shown in FIG. 3, a restrictor element 33 may be disposed in the upstream and downstream portions 12 or 14, such as but not limited to, a rigid ring member placed between coils 28, placed on an outside diameter of coils 28 or placed on an inside diameter of coils 28. The restrictor element 33 may be configured with a shape and size so as to prevent an expander device, such as but not limited to, a conventional balloon dilatation device, for example, from expanding either upstream or downstream portions 12 or 14 beyond a predefined amount. Restrictor element 33 may thus limit the expansion of either upstream or downstream portions 12 or 14 and help shape stent assembly 10.

The precise number of turns, diameters and other geometric characteristics of any of the coils 28 may vary depending upon the intended application. For small vessels, e.g., 3–5 mm inside diameter, as few as ten turns may be used to provide a stent assembly with sufficient filtration capability. In larger vessels, e.g., up to 3 cm, it may be desirable to employ a greater number of turns. It is understood that a greater or fewer number of turns may be employed depending upon the specific application, and the invention is not limited to any number of turns or coil geometry.

Figure 2:
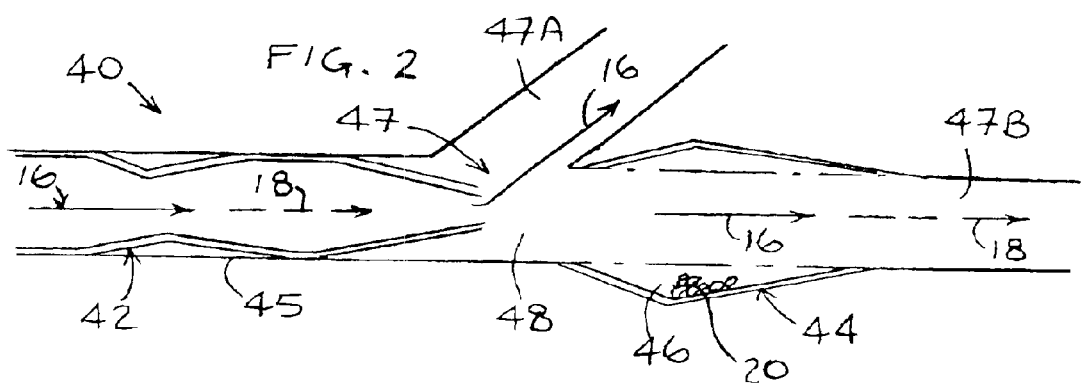
FIG. 2 is a simplified illustration of a stent assembly constructed in accordance with another embodiment of the present invention in a deployed state in a blood vessel with an intervening bifurcation.

Reference is now made to FIG. 2, which illustrates a stent assembly 40 constructed in accordance with an embodiment of the present invention. Stent assembly 40 preferably includes an upstream portion 42 and a downstream portion 44 in fluid communication with upstream portion 42. Downstream portion 44 preferably comprises a trapping region 46 for trapping therein embolic material 20.

Both upstream and downstream portions 42 and 44 are adapted for blood stream 16 to flow therethrough. Upstream portion 42 may be placed in a blood vessel 45 upstream of a bifurcation 47 in a blood vessel system. Bifurcation 47 may comprise a first downstream path 47A and a second downstream path 47B. Downstream portion 44 may be placed in second downstream path 47B. Downstream portion 44 is distanced from upstream portion 42 by a space 48. The space 48 is aligned with bifurcation 47 such that blood flows to both first and second downstream paths 47A and 47B with embolic material 20 being trapped in trapping region 46.

In both the embodiments of FIGS. 1 and 2, adequate storage volume may be provided in the trapping region (22 or 46, respectively) for storing therein embolic material 20. The embolic material 20 may be removed from the trapping region by a variety of methods, such as but not limited to, drawing or sucking the embolic material 20 out of the trapping region with a hypodermic needle.

In both the embodiments of FIGS. 1 and 2, the upstream and/or downstream portions may be coated with different materials to enhance the performance of the stent assembly. For example, the upstream and/or downstream portions may be coated or impregnated with an anti-thrombogenic agent, such as heparin. A biocompatible material may be attached to the interior of the trapping region to enhance the ability of the downstream portion to capture and retain embolic material 20. Alternatively, the upstream and/or downstream portions may comprise, such as be coated or impregnated with, a layer of fluid impermeable material or a friction, for example, polytetrafluoroethylene (PTFE) or polyurethane cloth. The fluid impermeable material may reduce turbulent flow through the stent assembly. This may be advantageous because too much turbulent flow may cause eddy currents and the like which may tend to draw embolic material 20 out of trapping region 22. Still alternatively, the upstream and/or downstream portions may comprise, such as being coated or impregnated with, a thrombogenic agent, to cause further clotting of material off the vessel or organ. As another alternative, the trapping region or any other portion of the upstream or downstream portions may comprise either a friction-enhancing material (wires, mesh, biological adhesive, for example) or a friction-reducing material (e.g., PTFE).

The present invention has been described hereinabove with reference to filtering fluids within blood vessels. However, it is appreciated that the present invention is not limited to this application. Rather the present invention is also suitable for many other applications, such as but not limited to, gastro-intestinal, respiratory, reproductive organ and urethral applications and elsewhere where is desirable to filter flow through an organ or vessel.

It will be appreciated by person skilled in the art that the present invention is not limited by what has been particularly shown and described herein above. Rather the scope of the present invention is defined only by the claims that follow:

What is claimed is:

1. A stent assembly comprising:

an upstream portion adapted to modify a flow characteristic of embolic material disposed in a blood stream flowing through said upstream portion; and a downstream portion in fluid communication and contiguous with said upstream portion and adapted for the blood stream to flow therethrough, said downstream portion comprising a trapping region for trapping therein said embolic material;

wherein said upstream portion comprises a downstream convergence that is asymmetric about a longitudinal axis of the upstream portion wherein the downstream convergence converges towards the longitudinal axis on one side thereof and on an opposite side thereof does not converge toward the longitudinal axis;

and said trapping region comprises a divergent portion that is asymmetric about the longitudinal axis comprising a region in which the divergent portion converges towards the longitudinal axis on one side thereof and on an opposite side thereof diverges away from the longitudinal axis.

2. The stent assembly according to claim 1, further comprising a restrictor element disposed in at least one of said upstream and downstream portions, said restrictor element being adapted to limit expansion of said at least one of said upstream and downstream portions.

* * * * *